United States Patent [19]

Dingwall et al.

[11] B 3,994,923

[45] Nov. 30, 1976

[54] 4-(3,5-DIALKYL-4-HYDROXYPHENYL)-1,2-DITHIOLE-3-THIONES

[75] Inventors: John Grey Dingwall, Brooklands Sale; Peter Miles; Donald Richard Randell, both of Stockport, all of England

[73] Assignee: Ciba-Geigy Corporation, Ardsley, N.Y.

[22] Filed: June 18, 1974

[21] Appl. No.: 480,452

[44] Published under the second Trial Voluntary Protest Program on February 10, 1976 as document No. B 480,452.

[30] Foreign Application Priority Data

June 20, 1973 United Kingdom............... 29334/73

[52] U.S. Cl................................ 260/327 C; 252/32; 252/33; 252/37.7; 252/47; 252/48.2
[51] Int. Cl.²......................................... C07D 339/04
[58] Field of Search ................................. 260/327 C

[56] References Cited

UNITED STATES PATENTS 2,653,910  9/1953  Airs et al. ............................. 252/45

FOREIGN PATENTS OR APPLICATIONS 808,064  1/1959  United Kingdom................... 252/45

OTHER PUBLICATIONS

Voronkov, et al., Chem. Abst. 73:77104b (1970).
Reid, Org. Chem. of Bivalent Sulfur, vol. II (1960, Chem. Pub. Co., N. Y.) p. 26.

*Primary Examiner*—Henry R. Jiles
*Assistant Examiner*—C. M. S. Jaisle
*Attorney, Agent, or Firm*—Luther A. R. Hall

[57] ABSTRACT

Novel 4-(3,5-dialkyl-4-hydroxyphenyl)-1,2-dithiole-3-thiones are used as additives for organic materials. They are prepared by reacting a corresponding alkylated phenol with sulfur and if necessary reacting the resulting compound with sodium disulphide and then with a corresponding halide.

26 Claims, No Drawings

4-(3,5-DIALKYL-4-HYDROXYPHENYL)-1,2-DITHIOLE-3-THIONES

The present invention relates to novel 4-(3,5-dialkyl-4-hydroxyphenyl)-1,2-dithiole-3-thiones.

According to the present invention there is provided a compound of the general formula:

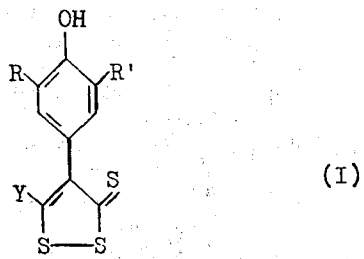

(I)

in which R and R¹ are the same or different and each is an alkyl radical having from 1 to 12 carbon atoms, a cycloalkyl radical having from 5 to 12 carbon atoms which may be substituted with alkyl groups having from 1 to 4 carbon atoms or an aralkyl radical having from 7 to 14 carbon atoms, and Y is hydrogen, mercapto or SR² where R² is an alkyl radical having from 1 to 20 carbon atoms, cycloalkyl having from 5 to 12 carbon atoms, alkenyl having from 3 to 20 carbon atoms, or aralkyl having from 7 to 14 carbon atoms.

Preferably R and R¹ are branched-chain alkyl radicals having from 3 to 8 carbon atoms, 1-methyl cyclohexyl or αα-dimethyl benzyl and Y is preferably hydrogen or a —S-alkyl group having from 6 to 18 carbon atoms.

Examples of compounds of formula I in which Y is hydrogen are:
 4-(3,5-di-isopropyl-4-hydroxyphenyl)-1,2-dithiole-3-thione
 4-(3,5-t-butyl-4-hydroxyphenyl)-1,2-dithiole-3-thione
 4-[3,5-bis(1,1-dimethylpropyl)-4-hydroxyphenyl]-1,2-dithiole-3-thione
 4-[3,5-bis(1,1-dimethylbutyl)-4-hydroxyphenyl]-1,2-dithiole-3-thione
 4-[3,5-bis(1,1,3,3-tetramethylbutyl)-4-hydroxyphenyl[-1,2-dithiole-3-thione
 4-[3,5-bis(1-methylcyclohexyl)-4-hydroxyphenyl[-1,2-dithiole-3-thione
 4-[3,5-bis(1,1-dimethylbenzyl)-4-hydroxyphenyl]-1,2-dithiole-3-thione
 4-(3-t-butyl-4-hydroxy-5-isopropylphenyl)-1,2-dithiole-3-thione
 4-(3-t-butyl-4-hydroxy-5-methylphenyl)-1,2-dithiole-3-thione
 4-[3-(1,1-dimethylpropyl)-4-hydroxy-5-isopropylphenyl[-1,2-dithiole-3-thione
 4-[3-(1,1-dimethylbenzyl)-4-hydroxy-5-isopropylphenyl]-1,2-dithiole-3-thione
 4-(3,5-di-sec-butyl-4-hydroxyphenyl)-1,2-dithiole-3-thione.

Examples of compounds of formula I in which Y is —SR² are
 5-benzylthio-4-(3,5-di-t-butyl-4-hydroxyphenyl)-1,2-dithiole-3-thione
 5-benzylthio-4-[3,5-bis(1,1-dimethylpropyl)-4-hydroxyphenyl]-1,2-dithiole-3-thione
 5-hexylthio-4-(3,5-di-t-butyl-4-hydroxyphenyl)-1,2-dithiole-3-thione
 5-hexylthio-4-[3,5-bis(1,1-dimethylbutyl)-4-hydroxyphenyl]-1,2-dithiole-3-thione
 5-octadecylthio-4-(3,5-di-t-butyl-4-hydroxyphenyl)-1,2-dithiole-3-thione
 5-octadecylthio-4[3,5-bis(1,1-dimethylbenzyl)-4-hydroxy-phenyl]-1,2-dithiole-3-thione
 5-allylthio-4-(3,5-di-t-butyl-4-hydroxyphenyl)-1,2-dithiole-3-thione
 5-cyclohexylthio-4-(3,5-di-t-butyl-4-hydroxyphenyl)-1,2-dithiole-3-thione The compounds of formula I in which Y is hydrogen may conveniently be prepared by reacting an alkylated phenol of the formula:

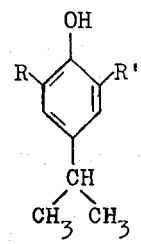

(II)

in which R and R¹ have the same significance as in formula I with sulphur in a refluxing solvent which is substantially inert under the conditions of the reaction and in the presence of a basic catalyst.

Suitable solvents are hydrocarbon solvents such as t-butylbenzene and 2,4,6-trimethylbenzene, chlorinated hydrocarbon solvents such as o-dichlorobenzene and dipolar aprotic solvents such as dimethylformamide. Suitable basic catalysts are inorganic bases such as potassium hydroxide and organic bases such as n-amylamine, di-n-amylamine, quinoline, isoquinoline and guanidines.

The compounds of formula II may be prepared by the alkylation of 4-isopropylphenol conveniently with an alcohol or olefin in the presence of an acid catalyst such as sulphuric acid and p-toluene sulphonic acid.

Compounds of the formula I in which Y is SR² may be prepared by alkylating a 5-mercapto-1,2-dithiole-3-thione of formula I wherein Y = SH with an alkyl, cycloalkyl, alkenyl or aralkyl halide in an ethanolic sodium ethoxide solution.

The intermediate 5-mercapto-1,2-dithiole-3-thiones of formula I wherein Y = SH may be prepared by reacting the corresponding 1,2-dithiole-3-thiones of formula I wherein Y = H with sodium disulphide solution in a suitable solvent such as dimethylformamide.

The compounds of formula I may be used alone or as a solution in a compound of formula II from which it is prepared. For instance, solutions containing from 10 to 90% and preferably 20 to 60% by weight of the compound of formula I may be used. When incorporated in lubricating oils the compounds of formula I impart wear resistant properties to metal surfaces. They are particularly useful as they are ashless. The compounds of formula I are also stabilisers for organic materials, especially lubricating oils and rubbers.

The present invention therefore also provides an organic material containing a functionally effective amount of a compound of formula I. When the organic material is a lubricating oil, this may be a mineral or synthetic oil or may be a mixture of mineral and synthetic lubricating oils, and may, if desired, be in the form of an emulsion.

The lubricating oils may contain an amount of the compound of formula I within the range of from 0.001 to 5% but preferably within the range of from 0.1 to 3% by weight based on the total weight of lubricating oil.

The lubricating oil, may, if desired, contain in addition other additives which are conventionally added to improve the properties thereof, such as antioxidants, metal passivators, rust inhibitors, viscosity index improvers/pour point depressants, dispersants/detergents and other extreme pressure/antiwear additives. Examples of antioxidants are:

a. Alkylated and non-alkylated aromatic amines and mixtures thereof, for example dioctyldiphenylamine;mono-t-octylphenyl-$\alpha$ and $\beta$-naphthylamines;phenothiazine; dioctylphenothiazine;phenyl-$\alpha$-naphthylamine; N,N'-di-sec-butyl p-phenylenediamine.
b. Hindered phenols, for example 2,6-ditertiarybutyl-p-cresol; 4,4'-bis-(2,6-diisopropylphenol); 2,4,6-triisopropylphenol; 2,2'-thio-bis-(4-methyl-6-tert-butylphenol); 4,4'-methylene bis (2,6-di-t-butyl-phenol).
c. Alkyl, aryl or alkaryl phosphites, for example trinonylphosphite; triphenylphosphite; diphenyldecylphosphite.
d. Esters of thiodipropionic acid or thiodiacetic acid, for example dilauryl thiodipropionate or dioctylthiodiacetate.
e. Salts of carbamic and dithiophosphoric acids, for example antimony diamyldithiocarbamate, zinc diamyldithiophosphate.
f. Metal salts, and metal complexes of organic chelating agents for example copper bis trifluoroacetylacetonates), copper phthalocyanines, tributyl ester of ethylenediamine tetra acetic acid mono sodium salt.
g. Free radical antioxidants for example nitroxides.
h. Combinations of two or more antioxidants from any of the above sections, for example an alkylated amine and a hindered phenol.

Examples of metal passivators are:
a. for copper, for example 1,2,4-triazoles, benzotriazole, tetrahydrobenzotriazole, 2,5-dimercaptothiadiazole, salicylidene-propylenediamine, salts of salicylaminoguanidine;
b. for magnesium, for example pyridylamines.
c. for lead, for example sebacic acid, quinizarin, propyl gallate.
d. Combination of two or more of the above additives. Examples of Rust Inhibitors are:

a. Organic acids, their esters, metal salts and anhydrides for example N-oleoyl sarcosine, sorbitan mono-oleate, lead naphthenate, dodecenylsuccinic anhydride.
b. Nitrogen containing materials, for example
  i. primary, secondary or tertiary aliphatic or cycloaliphatic amines and amine salts of organic and inorganic acids, for example morpholine, stearyl amine, triethanolamine caprylate.
  ii. Heterocyclic compounds, for example imidazolines, oxazolines.
c. Phosphorus containing materials, for example inorganic phosphates, phosphonic acids, amine phosphates.
d. Sulphur containing materials, for example barium dinonylnaphthalene sulphonates.
e. Combinations of two or more of the above additives. Examples of Viscosity Index Improvers/Pour Point Depressants are, for example: polyacrylates, polybutenes, polyvinyl pyrrolidones.

Examples of Dispersant/Detergents are, for example: metal sulphonates (Ca, Ba, Mg) and phenates, polybutenyl succinimides.

Examples of Extreme pressure/Antiwear additives are:
sulphur and/or phosphorus and/or halogen containing materials, for example sulphurised sperm oil, zinc dialkyl phosphoro dithioates, tritolyl-phosphate, chlorinated paraffins.

The present invention also provides a process of producing composition of organic materials, e.g. lubricating oils comprising a functionally effective proportion of a compound having formula I, which comprises admixing the lubricating oil with the compound having the formula I.

The following Examples further illustrate the present invention. Parts by weight bear the same relation to parts by volume as do kilograms to litres. Parts and percentages are expressed by weight unless otherwise stated and "°" are "°C".

EXAMPLE 1

356 parts of 2,6-di-t-butyl-4-isopropyl phenol and 275 parts of sulphur were heated at reflux in 1000 parts o-dichlorobenzene for 55 hours in the presence of 3.5 parts isoquinoline. On cooling 4-(3,5-di-t-butyl-4-hydroxyphenyl)-1,2-dithiole-3-thione (276 parts) crystallised out as dark brown prisms, m.p. 257°–258°. The analysis was as follows:

|  | Required for $C_{17}H_{22}OS_3$ | Found |
|---|---|---|
| Carbon | 60.4% | 60.3% |
| Hydrogen | 6.5% | 6.4% |
| Sulphur | 28.4% | 28.3% |

EXAMPLES 2–7

By following essentially the same procedure to that described in Example 1, but using instead of the phenol there used, the phenols listed in table I, the corresponding 1,2-dithiole-3-thiones were obtained.

Table I

| | Formula II | | | Formula I | | | | Melting |
| Example | R | R' | Parts | R | R' | Y | Parts | Point |
|---|---|---|---|---|---|---|---|---|
| 2 | —C(CH$_3$)$_2$C$_2$H$_5$ | —C(CH$_3$)$_2$C$_2$H$_5$ | 25.7 | —C(CH$_3$)$_2$C$_2$H$_5$ | —C(CH$_3$)$_2$C$_2$H$_5$ | H | 16 | 184° |
| 3 | —C(CH$_3$)$_2$C$_3$H$_7$ | —C(CH$_3$)$_2$C$_3$H$_7$ | 22.2 | —C(CH$_3$)$_2$C$_3$H$_7$ | —C(CH$_3$)$_2$C$_3$H$_7$ | H | 9.0 | 103° |

Table I-continued

| Example | Formula II R | R' | Parts | Formula I R | R' | Y | Parts | Melting Point |
|---|---|---|---|---|---|---|---|---|
| 4 | Me  | Me  |  | Me | Me | H | 1.8 | 175° |
| 5 | —CH(CH$_3$)$_2$ | —CH(CH$_3$)$_2$ | 55 | —CH(CH$_3$)$_2$ | —CH(CH$_3$)$_2$ | H | 9 | 127–30° |
| 6 | —CH(CH$_3$)$_2$ | —C(CH$_3$)$_3$ | 15.4 | —CH(CH$_3$)$_2$ | —C(CH$_3$)$_3$ | H | 3.2 | 154.5° |
| 7 | —C(CH$_3$)$_2$Ph | —C(CH$_3$)$_2$—Ph | 12.2 | —C(CH$_3$)$_2$Ph | —C(CH$_3$)$_2$Ph | H | 6.2 | 166–9° |

| Example | Analysis Calculated % |  |  | Found % |  |  |
|---|---|---|---|---|---|---|
|  | C | H | S | C | H | S |
| 2 | 62.4 | 7.1 | 26.3 | 62.4 | 7.0 | 26.3 |
| 3 | 64.0 | 7.6 | 24.4 | 64.2 | 7.4 | 24.3 |
| 4 | 66.0 | 7.2 | 23.0 | 66.2 | 7.2 | 23.1 |
| 5 | 58.1 | 5.8 | 30.9 | 58.3 | 6.1 | 29.2 |
| 6 | 65.7* | 6.5* | 23.9* | 65.4 | 6.2 | 24.6 |
| 7 | 70.2 | 5.6 | 20.8 | 70.3 | 5.8 | 21.0 |

Ph denotes the phenyl residue
*calculated 1 molecule benzene of recrystallization

EXAMPLE 8

22 parts of 2,4,6-triisopropylphenol and 9.6 parts of sulphur were heated at reflux in 60 parts o-dichlorobenzene for 111 hours in the presence of 0.22 parts quinoline. The o-dichlorobenzene was then distilled off under vacuum. The residue was a brown viscous liquid containing 10.5% sulphur. Thin layer chromatography comparison with the product of Example 5 showed the presence of a substantial amount of 4-(3,5-di-isopropyl-4-hydroxyphenyl)-1,2-dithiole-3-thione.

EXAMPLE 9

22 parts of a mixture of isopropylated phenols containing 80% 2,4,6-triisopropylphenol and 20% 2,4,5-triisopropylphenol and 4.8 parts of sulphur were heated at reflux in 60 parts o-dichlorobenzene for 107 hours in the presence of 0.22 parts quinoline. The o-dichlorobenzene was then distilled off under vacuum. The residue was a brown viscous liquid containing 5.8% sulphur. Thin layer chromatography comparison with the product of Example 5 showed the presence of a substantial amount of 4-(3,5-di-isopropyl-4-hydroxyphenyl)-1,2-dithiole-3-thione.

EXAMPLE 10

40 parts of a mixture of propylated sec-butyl phenols containing 82.6% 2,6-di-sec-butyl-4-isopropylphenol and 25.5 parts of sulphur were heated at reflux in 112 parts o-dichlorobenzene for 50 hours in the presence of 0.65 parts quinoline. The o-dichlorobenzene was then distilled off under vacuum. The residue was a black viscous liquid. 20 parts of this residue were chromatographed on a silica column using toluene as eluant. The main fractions produced 8.8 parts of a dark red liquid containing 21.8% sulphur. Nuclear magnetic resonance spectroscopy showed that the major component of this liquid was 4-(3,5-di-sec-butyl-4-hydroxyphenyl)-1,2-dithiole-3-thione.

EXAMPLE 11

33.8 parts of 4-(3,5-di-t-butyl-4-hydroxyphenyl)-1,2-dithiole-3-thione and 40 parts of a 2.5 molar solution of sodium disulphide were dissolved in 40 parts of dimethylformamide and warmed at 100°C for 15 minutes. 500 parts of water were then added, the mixture extracted several times with ether to remove any starting material, and then 60 parts of 3N hydrochloric acid solution were added slowly with stirring. The solid was filtered giving 27 parts of 5-mercapto-4-(3,5-di-t-butyl-4-hydroxyphenyl)-1,2-dithiole-3-thione m.p. 182°C which gave the following elemental analysis:

|  | Required for C$_{17}$H$_{22}$OS$_4$ | Found |
|---|---|---|
| Carbon | 55.1% | 54.6% |
| Hydrogen | 6.0% | 6.2% |
| Sulphur | 34.6% | 33.6% |

EXAMPLE 12

0.92 parts of sodium was dissolved in 80 parts of ethanol and to this was added 14.8 parts of 5-mercapto-4-(3,5-di-t-butyl-4-hydroxyphenyl)-1,2-dithiole-3-thione, as prepared in example 11 dissolved in 200 parts ethanol. The mixture was then warmed to 50°C and a solution of 6.6 parts n-hexyl bromide in 50 parts ethanol was added dropwise. The mixture was refluxed for 5 hours, the ethanol evaporated, and the residue extracted with diethyl ether. Evaporation of the ether solution gave a crystalline residue which was crystallised from ether to give 12 parts of 5-n-hexylthio 4-(3,5-di-t-butyl-4-hydroxyphenyl)-1,2-dithiole-3-thione, m.p. 110°.

EXAMPLE 13

When the reaction described in Example 12 was carried out using 14.2 parts n-octadecyl bromide in place of the n-hexyl bromide the product was 23.2 parts of 5-n-octadecylthio-4-(3,5-di-t-butyl-4-hydroxy phenyl)-1,2-dithiole-3-thione, m.p. 76°C, which gave the following elemental analysis:

|  | Required for C$_{35}$H$_{58}$OS$_4$ | Found |
|---|---|---|
| Carbon | 67.5 | 67.3 |
| Hydrogen | 9.4 | 9.5 |
| Sulphur | 20.6 | 20.9 |

EXAMPLE 14

When the reaction described in Example 12 was carried out using 6.8 parts benzyl bromide instead of n-hexyl bromide the product was 7.6 parts of 5-benzylthio-4-(3,5-di-t-butyl-4-hydroxyphenyl)-1,2-dithiole-3-thione, m.p. 165°–6°C. Which gave the following elemental analysis:

Required for C$_{24}$H$_{48}$OS$_4$    Found

|          | -continued |       |
|----------|-----------|-------|
| Carbon   | 62.6%     | 62.9% |
| Hydrogen | 6.1%      | 6.2%  |

The following Examples 15 to 18 illustrate methods of preparation of Compounds of formula II.

EXAMPLE 15

38 parts of para-isopropyl phenol and 74 parts of t-amyl alcohol in 100 parts benzene were refluxed 16 hours with 1.5 parts concentrated sulphuric acid as catalyst, the water formed being continuously removed from the reaction. The benzene solution was evaporated, the residue dissolved in ether, washed with water, Claisen solution and then washed neutral with water. The ether solution was then evaporated and the residue purified by filtration trough a column of silica gel (800g) using petroleum ether as solvent, to give 34 parts of 2,6-di-t-amyl-4-isopropylphenol as a colourless oil $n_D^{20}$ 1,4961, $v$max 3625 cm (—OH) which gave the following elemental analysis:

|          | Required for $C_{19}H_{32}O$ | Found |
|----------|------------------------------|-------|
| Carbon   | 82.5%                        | 82.8% |
| Hydrogen | 11.7%                        | 11.7% |

EXAMPLE 16

38 parts of para-isopropylphenol and 96 grams 1-methylcyclohexanol were reacted as described in Example 15 to give 2,6-bis (1-methyl-cyclohexyl)-4-isopropylphenol, $\gamma$max 3620 cm$^{-1}$ (—OH).

EXAMPLE 17

38 parts of para-isopropylphenol and 1.5 parts of concentrated sulphuric acid were mixed and heated to 70°C. 70.5 parts of propylene dimer (essentially 2-methylpent-1-ene) were added dropwise over 2 hours and the mixture then stirred at 70° for 3 hours.

The mixture was worked up as described in Example 15 to give 2,6-bis(1,1-dimethylbutyl)-4-isopropylphenol, $n_D^{20}$ =1.4900, $v$max 3625 cm$^{-1}$ (—OH) which gave the following elemental analysis:

|          | Required for $C_{21}H_{36}O$ | Found  |
|----------|------------------------------|--------|
| Carbon   | 82.84%                       | 82.74% |
| Hydrogen | 11.95%                       | 11.70% |

EXAMPLE 18

38 parts of para-isopropylphenol and 132 parts of α-methylstyrene were heated and stirred at 135°–145° for 8 hours in presence of lg p-toluene sulphonic acid as catalyst. The mixture was dissolved in ether, washed with water, then Claisen solution, then finally with water and dried. Evaporation of the ether yielded an oil which was dissolved in an equal volume of ethanol and cooled to give 2,6-bis (1,1-dimethylbenzyl)-4-isopropylphenol, mp.92°C which gave the following elemental analysis:

|          | Required for $C_{27}H_{32}O$ | Found |
|----------|------------------------------|-------|
| Carbon   | 87.0%                        | 86.8% |
| Hydrogen | 8.7%                         | 8.7%  |

EXAMPLE 19

The following Example illustrates the use of the compounds of formula I of the present invention as extreme pressure additives for lubricating oils.

The Falex Test, an extreme pressure test for fluid lubricants was carried out in accordance with Method A of the Institute of Petroleum Standard Part I No. 241/69T, but modified to use 100 pound (=45,36 kg) incremental loads.

Nine samples of an HVI 160 oil were used, one containing no additive, and eight containing the products of Examples 1, 2, 3, 7, 9, 12, 13 and 14. The results are shown in Table I.

Table I

| Additive Used        | Concentration | Failure Load (kg) |
|----------------------|---------------|-------------------|
| None                 |               | 408               |
| Product of Example 1 | 0.2%          | 635               |
| Product of Example 2 | 0.2%          | 499–544           |
| Product of Example 3 | 0.2%          | 544               |
| Product of Example 7 | 0.2%          | 499               |
| Product of Example 9 | 0.2%          | 567               |
| Product of Example 12| 0.2%          | 590               |
| Product of Example 13| 0.2%          | 499               |
| Product of Example 14| 0.2%          | 544               |

EXAMPLE 20

This example illustrates the use of the compounds of formula I as antioxidants.

The CERL Turbine Oil oxidation test was carried out by incorporating into 25 ml of an HVI 65 oil (having a viscosity of 33.3 centistokes at 38°C) 0.5% by weight of a compound of the formula I based on the weight of oil and maintaining the oil at 120°C for 7 days in the presence of metallic copper, oxygen being passed through at a flow rate of 1 litre per hour. The insoluble sludge was filtered off, washed, dried and weighed. The tube was washed with chloroform, the chloroform extract evaporated and the residue weighed. The total sludge was thus determined from the two weighings. The acidity increase of the filtered oil was determined potentiometrically and added to the determination of the volatile acidity produced during the test and condensed in 25 ml of water at room temperature. The same procedure was followed eight times, using the products shown in the following Table II.

Table II

| Additive Used         | Concentration % | Total Sludge (mg) | Acid Value Increase (mg KOH per g) |
|-----------------------|-----------------|-------------------|-------------------------------------|
| None                  |                 | 0.82              | 2.27                                |
| Product of Example 1  | 0.5             | 0.14              | 1.17                                |
| Product of Example 2  | 0.5             | 0.45              | 0.63                                |
| Product of Example 3  | 0.5             | 0.56              | 0.70                                |
| Product of Example 5  | 0.5             | 0.27              | 0.46                                |
| Product of Example 7  | 0.5             | 0.34              | 0.52                                |
| Product of Example 12 | 0.5             | 0.38              | 0.70                                |
| Product of Example 13 | 0.5             | 0.34              | 0.54                                |
| Product of Example 14 | 0.5             | 0.35              | 0.56                                |

EXAMPLE 21

The Petter Wl Test, an oil oxidation and bearing corrosion test was carried out using the Petter Wl spark ignition test engine. The details are given in the Institute of Petroleum Standards Part 3 No. 176/69. 0.5% by weight of a compound of formula I and also 1% by weight of a commercially available zinc dialkyldithiophosphate were incorporated into a 500 solvent neutral oil.

TABLE III

| Additive used | Concentration | % visc. increase | Acid value increase (mg KOH per g) | Bearing weight loss mg. | Piston skirt rating |
|---|---|---|---|---|---|
| Product of Example 1 | 0.5 % | 1.0 | 0.15 | 3 | 10 |
| A zinc dialkyl dithiophosphate | 1.0 % | 2.1 | Neg. | 37 | 8 |

The above figures indicate that the product of Example 1 has better cleanliness, antioxidant and bearing corrosion inhibition properties when compared with a commercially available zinc dialkyldithiophosphate at double the concentration.

What we claim is:
1. A compound of the formula

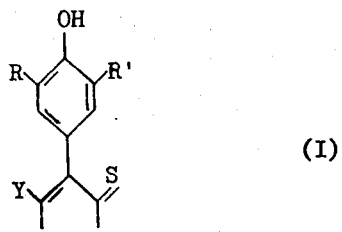

(I)

in which R and R¹ are the same or different and each is an alkyl radical having from 1 to 12 carbon atoms, a cycloalkyl radical having from 5 to 12 carbon atoms which may be substituted with alkyl groups having from 1 to 4 carbon atoms or an aralkyl radical having from 7 to 14 carbon atoms, and Y is hydrogen, mercapto or SR² where R² is an alkyl radical having from 1 to 20 carbon atoms, cycloalkyl having from 5 to 12 carbon atoms, alkenyl from 3 to 20 carbon atoms, or aralkyl having from 7 to 14 carbon atoms.

2. A compound as claimed in claim 1 in which R and R¹ are branched-chain alkyl radicals having from 3 to 8 carbon atoms, 1-methyl cyclohexyl or αα-dimethyl benzyl.

3. A compound as claimed in claim 1 in which Y is an -S-alkyl group having from 6 to 18 carbon atoms.

4. A compound as claimed in claim 1 which is 4-(3,5-di-isopropyl-4-hydroxyphenyl)-1,2-dithiole-3-thione.

5. A compound as claimed in claim 1 which is 4-((3,5-di-t-butyl-4-hydroxyphenyl)-1,2-dithiole-3-thione.

6. A compound as claimed in claim 1 which is 4-[3,5-bis(1,1-dimethylpropyl)-4-hydroxyphenyl]-1,2-dithiole-3-thione.

7. A compound as claimed in claim 1 which is 4-[3,5-bis(1,1-dimethylbutyl)-4-hydroxyphenyl]-1,2-dithiole-3-thione.

8. A compound as claimed in claim 1 which is 4-[3,5-bis(1,1,3,3-tetramethylbutyl)-4-hydroxyphenyl]-1,2-dithiole-3-thione.

9. A compound as claimed in claim 1 which is 4-[3,5-bis(1-methylcyclohexyl)-4-hydroxyphenyl]-1,2-dithiole-3-thione.

10. A compound as claimed in claim 1 which is 4-[3,5-bis(1,1-dimethylbenzyl)-4-hydroxyphenyl]-1,2-dithiole-3-thione.

11. A compound as claimed in claim 1 which is 4-(3-t-butyl-4-hydroxy-5-isopropylphenyl)-1,2-dithiole-3-thione.

12. A compound as claimed in claim 1 which is 4-(3-t-butyl-4-hydroxy-5-methylphenyl)-1,2-dithiole-3-thione.

13. A compound as claimed in claim 1 which is 4-[3-(1,1-dimethylpropyl)-4-hydroxy-5-isopropylphenyl]-1,2-dithiole-3-thione.

14. A compound as claimed in claim 1 which is 4-[3-(1,1-dimethylbenzyl)-4-hydroxy-5-isopropylphenyl]-1,2-dithiole-3-thione.

15. A compound as claimed in claim 1 which is 5-benzylthio-4-(3,5-di-t-butyl-4-hydroxyphenyl)-1,2-dithiole-3-thione.

16. A compound as claimed in claim 1 which is 5-benzylthio-4-[3,5-bis(1,1-dimethylpropyl)-4-hydroxyphenyl]-1,2-dithiole-3-thione.

17. A compound as claimed in claim 1 which is 5-hexylthio-4-(3,5-di-t-butyl-4-hydroxyphenyl)-1,2-dithiole-3-thione.

18. A compound as claimed in claim 1 which is 5-hexylthio-4-[3,5-bis(1,1-dimethylbutyl)-4-hydroxyphenyl]-1,2-dithiole-3-thione.

19. A compound as claimed in claim 1 which is 5-octadecylthio-4-(3,5-di-t-butyl-4-hydroxyphenyl)-1,2-dithiole-3-thione.

20. A compound as claimed in claim 1 which is 5-octadecylthio-4-[3,5-bis(1,1-dimethylbenzyl)-4-hydroxyphenyl]-1,2-dithiole-3-thione.

21. A compound as claimed in claim 1 which is 5-allylthio-4-(3,5-di-t-butyl-4-hydroxyphenyl)-1,2-dithiole-3-thione.

22. A compound as claimed in claim 1 which is 5-cyclohexylthio-4-(3,5-di-t-butyl-4-hydroxyphenyl)-1,2-dithiole-3-thione.

23. A compound as claimed in claim 1 which is 4-(3,5-di-sec-butyl-4-hydroxyphenyl)-1,2-dithiole-3-thione.

24. A process of preparing a compound of claim 1 in which Y is hydrogen by reacting an alkylated phenol of the formula

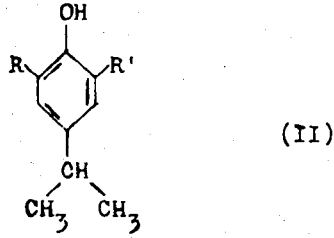

(II)

in which R and R¹ have the meanings indicated in claim 1 with sulphur in a refluxing solvent which is substantially inert under the conditions of the reaction and in the presence of a basic catalyst.

25. A process as claimed in claim 24 in which the solvent is t-butylbenzene, 2,4,6-trimethylbenzene, o-dichlorobenzene or dimethylformamide.

26. A process as claimed in claim 24 in which the basic catalyst is potassium hydroxide, n-amylamine, di-n-amylamine, quinoline, isoquinoline or a guanidine.

* * * * *